United States Patent [19]
Choudhury et al.

[11] Patent Number: 5,626,179
[45] Date of Patent: May 6, 1997

[54] PROCESS FOR MANUFACTURE OF CASTINGS OF REACTIVE METALS

[75] Inventors: Alok Choudhury, Püttlingen; Matthias Blum, Büdlingen; Harald Scholz, Rodenbach; Georg Jarczyk, Grosskrotzenburg, all of Germany

[73] Assignee: Ald Vacuum Technologies GmbH, Erlensee, Germany

[21] Appl. No.: 458,904

[22] Filed: Jun. 2, 1995

[30] Foreign Application Priority Data

Jun. 9, 1994 [DE] Germany ............................ 44 20 138.9
Feb. 20, 1995 [DE] Germany ............................ 195 05 689.2

[51] Int. Cl.$^6$ .............................. B22C 1/00; B22C 3/00
[52] U.S. Cl. ...................... 164/66.1; 164/114; 164/138; 164/529; 249/135; 106/38.27; 106/38.9
[58] Field of Search ............................ 164/138, 418, 164/459, 114, 66.1, 121, 529, 520, 523, 524; 106/38.22, 38.27, 38.9; 249/135

[56] References Cited

U.S. PATENT DOCUMENTS

| | | | |
|---|---|---|---|
| 2,028,911 | 1/1936 | Marvin | 164/114 |
| 2,912,731 | 11/1959 | Brennan et al. | 164/121 |
| 3,268,963 | 8/1966 | Mann | 164/66.1 |
| 3,339,588 | 9/1967 | Nilles | 164/138 |
| 3,420,291 | 1/1969 | Chandley et al. | 164/66.1 |
| 3,990,498 | 11/1976 | Dompas et al. | 164/459 |
| 4,240,494 | 12/1980 | Kryanin et al. | 164/66.1 |
| 5,119,865 | 6/1992 | Mae et al. | 164/114 |

FOREIGN PATENT DOCUMENTS

| | | |
|---|---|---|
| 6487050 | 3/1989 | Japan . |
| 5285624 | 11/1993 | Japan . |

*Primary Examiner*—K. Y. Lin
*Attorney, Agent, or Firm*—Felfe & Lynch

[57] ABSTRACT

In the production of castings from a melt of a reactive metal selected from the group consisting of titanium, titanium alloys, and titanium-based alloys, a reusable casting mold (20) is used; the mold, at least in the area of the surface which comes in contact with the melt, consists of at least one metal selected from the group consisting of tantalum, niobium, zirconium, and/or their alloys. The casting mold (20) preferably consists, at least in the area of the surface which comes in contact with the melt, of a tantalum based alloy containing at least 50 wt. % of tantalum. The casting molds can be made of a homogeneous metal, but it is also possible to insert shells of the metals in question into a base body to form the boundaries of the mold cavities, whereas the base body itself consists of some other metal or alloy or of a nonmetal such as graphite or silicon nitride. Insofar as the casting molds in question are molds for centrifugal casting, it is preferable to use titanium, a titanium alloy, or titanium aluminide as the nonmetal for the base body.

13 Claims, 4 Drawing Sheets

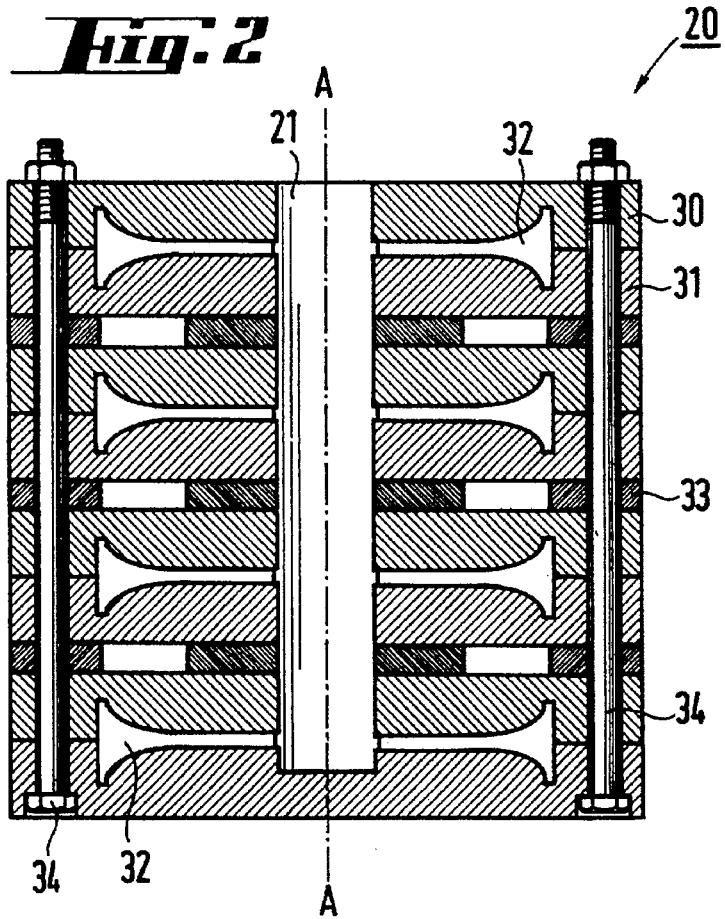
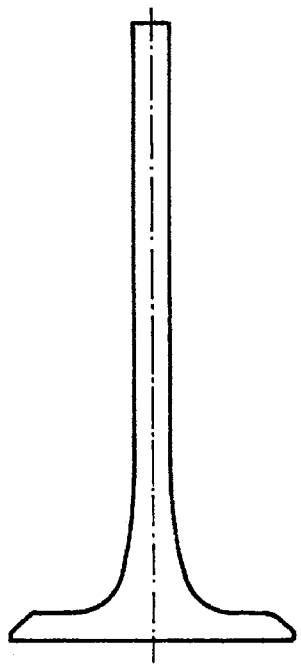
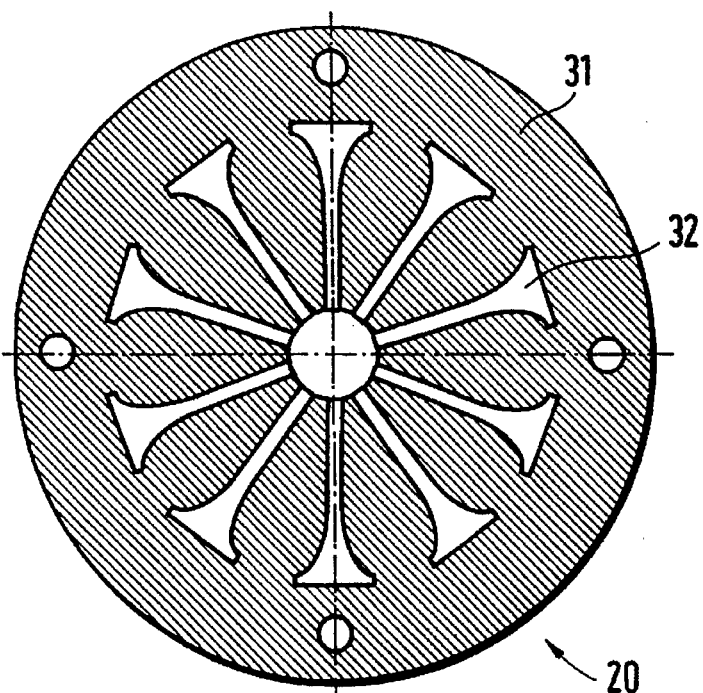
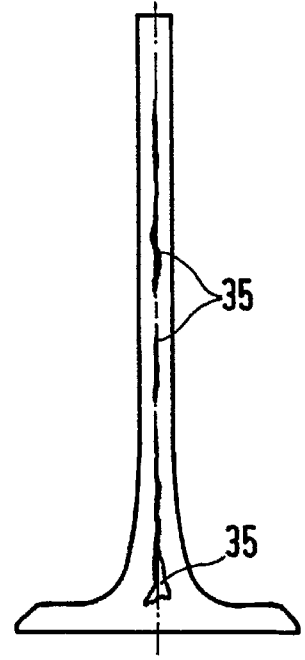

PROCESS FOR MANUFACTURE OF CASTINGS OF REACTIVE METALS

BACKGROUND OF THE INVENTION

The invention pertains to a process for the production of castings of a melt of a reactive metal from the group consisting of titanium, titanium alloys, and titanium-based alloys in a reusable casting mold.

There is an increasing demand for structural components of titanium and alloys containing considerable amounts of titanium, because these materials have a low specific gravity and are nevertheless extremely strong, provided that the specific properties of titanium, including its high melting point and its reactivity at high temperatures, are taken into account sufficiently. At its melting temperature, titanium reacts not only with reactive gases, including oxygen in particular, but also with oxides and nearly all types ceramics, because ceramics usually consist at least primarily of oxide compounds. Because of the great affinity of titanium for oxygen, oxygen is taken away from the oxides, which leads to the formation of titanium oxides. Some materials which have been found to give excellent results in certain areas of application are listed below by way of example:

pure titanium,

Ti 6 Al 4 V,

Ti 6 Al 2 Sn 4 Zr 2 Mo,

Ti 5 Al 2.5 Sn,

Ti 15 V 3 Al 3 Cr 3 Sn,

Ti Al 5 Fe 2.5,

50 Ti 46 Al 2 Cr 2 Nb, and titanium aluminides.

The use of titanium aluminides, e.g., TiAl, as a material for numerous components deserves special mention. Because of their low density, relatively high strength at high temperatures, and corrosion resistance, the titanium aluminides are considered the optimum material for various areas of application. Because these materials are very difficult to work, the only way to shape them is by casting. Especially in conjunction with casting, however, titanium-containing metals present further problems, which will be discussed in greater detail below.

Some examples of the use of titanium-containing materials are listed here:

valves for internal combustion machines, turbine wheels and turbine vanes, compressor rotors, biomedical prostheses (implants), and compressor housings in aircraft construction.

Especially in the area of motor vehicle racing, both intake and exhaust valves made of certain titanium alloys have been found to yield excellent results. Thought is therefore now being given to the general use of such valves in internal combustion machines of all types.

In the article by Schädlich-Stubenrauch et al. entitled "Numerical simulation of the alpha case as a quality criterion for the investment casting of small, thin-walled titanium parts," published at the Sixth World Conference on Titanium, France 1988, pp. 649–654, the problems which arise when titanium alloys are cast into molds of oxide materials are described. Titanium oxides form on the surface of the casting, but in addition oxygen also goes into solution at the grain boundaries at the rate of as much as 10 wt. %. It is therefore necessary to refinish the surfaces of the casting, which can be done either chemically or by cutting away the material. Of necessity, the thickness of the oxygen-containing surface layer increases with the length of the cooling period, which limits the use of molds of oxide materials for thin-walled workpieces. In addition, it is stated that it is advisable to subject the finished workpieces afterwards to a hot isostatic pressing step (HIP process). As a result, the cost of such components increases quite dramatically. The article studies these relationships on the basis of wedge-shaped castings.

The article by Tsutomu Oka et al. entitled "Manufacturing of automotive engine valves by plasma package melting of scrap titanium," published at the Sixth World Conference on Titanium, France, 1988, pp. 621–626, tells us that the valves used in internal combustion engines can be made of titanium alloys. For the production of the intake valves, which operate at relatively low temperatures of up to about 450° C., the alloy Ti 6 Al 4 V is recommended. For the exhaust valves, the operating temperatures of which can be as high as 700° C. or more, the alloy Ti 6 Al 2 Sn 4 Zr 2 Mo 0.1 Si is recommended, in which case it is pointed out that it is difficult to produce parts with a diameter of less than 10 mm because of the difficulty of machining this material. It is therefore recommended that, for these exhaust valves, the valve plates be made of the latter titanium alloy and that it be combined with valve shafts made of Ti 6 Al 4 V. This article also demonstrates the circuitous routes which must be taken to work around the material properties of certain titanium alloys during processing Through the article by Zwicker et al. entitled "Evaluation of centrifugally cast TiAl5Fe2.5 alloy for implant material", it is known that hip joint prostheses or implants can be produced from the titanium alloy cited in the title in a copper mold by means of a centrifugal casting process. It is stated that, as a result of the fast quenching rate attributable to the copper, the advantage of a fine-grained surface is obtained; it is also pointed out, however, that the fast cooling rate leads to the formation of pores caused by gas inclusions and to the formation of shrink holes, which lead to a notch effect. It is therefore recommended that the pores and shrink holes be eliminated by a HIP process, although it is expressly pointed out that, even at a pressure of 1,000 bars, it is possible to close only small pores and shrink holes, not pores at the surface of the workpiece, which are in fact opened even wider by the pressure and which intensify the notch effect even more. To correct these defects, it is stated that the surface irregularities be closed by welding, as a result of which, however, the disadvantage of a coarse grain structure is obtained in return. As the parameters for the HIP process, it is stated that a pressure of 1,000 bars should be allowed to act for 3 hours at 950° C. The article contains the further suggestion that the copper mold must have a relatively high weight in comparison to that of the workpiece to avoid reactions between the liquid titanium alloy and the surface of the copper. This suggestion allows the single conclusion that the copper mold must be used in the cold state and that therefore any preheating of the copper mold must be omitted, which is associated in turn with an undesirably fast quenching rate.

It can be derived from the state of the art sketched above that extremely strict requirements must be imposed on the selection of the mold material, that is, of the material used for the casting mold, and that, in addition, narrowly defined processing guidelines must be followed in order to prevent damage to the workpiece or to the chill form or casting mold. In a sense, therefore, the properties of the melt and those of the casting mold are diametrically opposed, and it should also be remembered that most titanium alloys must be cast at temperatures which are significantly above 1,500° C., whereas copper has a melting point of 1,084° C., and the eutectic point of the alloy copper/titanium is 865° C.

U.S. Pat. No. 5,119,865 deals with the problem of improving the dimensional accuracy or accuracy of shape of centrifugal casting molds of copper and the ease with which workpieces of titanium alloys can be removed from the mold. According to this patent, zirconium, chromium, beryllium, cobalt, and silver are added to the copper as alloying elements, the sum of all the alloying elements not exceeding 3 wt. %. A comparison example, in which the copper was alloyed with 18 wt. % of nickel, did not lead to success. The patent deals with the electrical conductivity of the material, not with its thermal conductivity, so that the problems of a fast quenching rate and of the formation of pores and shrink holes were not discussed. On the other hand, this patent does discuss the disadvantages of ceramic or oxide mold materials.

From the articles by:

1. Krone: "Production and properties of precision and compact castings of titanium materials", published in Giesserei 65, No. 20, pp. 540–549, Sept. 28, 1978; and 2. Krone et al.: "Titanium castings: manufacture and properties," published in AFS International Cast Metals Journal, Vol. 2, No. 1, pp. 37–40, Mar. 1977, we know that precision casting molds can be produced with a "metallic front layer", although these molds are so-called "lost" molds, used according to the lost wax method for a single use. Nonmetallic materials, primarily oxides, are present behind the metallic front layer. The metallic front layer is again made from a paste (slurry) and fired, this paste consisting of a mixture of metal powders, including tungsten, tantalum, niobium, and/or molybdenum powders together with inhibitor formers and liquid organometal compounds. This layer therefore contains significant amounts of nonmetallic constituents. The entire mold is then supposed to be removed by water jets, airless blast cleaning, sandblasting, etc., from the castings, which it is still necessary to clean afterwards by the use of salt baths and manual treatment. This works only because the front layer does not have a high degree of cohesiveness in itself as a result of the presence of nonmetallic materials in it.

A disadvantage is that the front layer cannot prevent the uptake of oxygen into the castings, because, first, the front layer itself contains oxygen compounds; second, because it is permeable to oxygen coming from the ceramic mass behind it; and, third, because in particular it reaches a very high temperature especially during the casting operation, which promotes the migration of oxygen.

SUMMARY OF THE INVENTION

According to the invention, castings of titanium or titanium alloys can be obtained which have a smooth surface without incorporated oxygen and which are free of shrink holes and other cavities, so that the need for complicated finishing treatments to correct the known defects can be eliminated entirely or at least nearly so.

This is accomplished by using a casting mold which consists, at least in the area of the surface which comes in contact with the melt, of at least one metal, free of nonmetallic constituents, selected from the group consisting of tantalum, niobium, zirconium, and/or their alloys.

Through the use of a casting mold of this type, it is impossible for any reaction to occur between the material of the mold and the material of the casting, and the partial melting of the surface of the mold cavity under the action of the heat of the melt is excluded even if the casting mold already has a temperature considerably above 800° C. before the casting operation.

In addition, through the use of metals selected from the group tantalum, niobium, zirconium, and/or their alloys, a much slower quenching rate is achieved, because these materials have much lower thermal conductivities. For example, the thermal conductivities of tantalum and niobium are 14% and 13%, respectively, of the thermal conductivity of copper; and the thermal conductivity of zirconium is only 6% of that of copper. The specific heat capacity of the cited mold materials is also significantly lower than that of copper. For example, the specific heat capacity of tantalum is 36% of the comparable value for copper, and the specific heat capacities of the materials niobium and zirconium are 70% and 72% respectively, of the comparable value for copper. Especially in their association with one another, these properties lead to a significant slowdown in the cooling of the castings. As a result, it is no longer necessary to fear the formation of a hard shell with shrink holes and pores in the interior. The melt has sufficient time to follow flow as the casting shrinks during cooling and solidification.

As a result of the selection of materials according to the invention, the need to subject the surface of the workpiece to finishing treatments, whether by the removal of the boundary layer, by local welding work, or even by a finishing compaction of the workpieces by the so-called HIP process, is eliminated either entirely or at least nearly so. In the case of valves for internal combustion engines, there is also no longer any need to assemble the valve from a plate and a shaft of different materials simply because the processing of these materials is so difficult.

It is not mandatory that the casting mold consist entirely of the selected materials; on the contrary, in the limit case it is necessary merely that the surface which comes in contact with the melt be made of the cited metals or their alloys. In the limit case, a layer thickness of only 2 mm is sufficient. A surface of this type is referred to in the following as a "shell".

The use of a tantalum-based alloy is especially advantageous in this case.

The process according to the invention makes it possible in particular to produce satisfactory castings by the centrifugal casting method.

The quenching rate can be reduced even more by preheating the casting mold before the casting operation; the preheating temperature is adjusted to a value below the liquidus temperature of the melt to be cast. It is especially advantageous in this case for the preheating temperature to be between 800° C. and the solidus temperature of the melt to be cast.

With respect to the defect-free formation of the castings, it is especially advantageous for the operation of casting the melt into the mold to be carried out in a closed mold chamber at a pressure of less than 100 mbars, preferably of less than 10 mbars.

Conversely, to increase the cooling rate of the casting mold after the casting operation or after the solidification of the castings, it is especially advantageous to introduce an inert gas, preferably at least one noble gas from the group argon and helium, into the mold chamber to reduce the cycle time.

The higher the pressure of the inert gas in the mold chamber, the faster the cooling rate, under the assumption that the casting mold is kept in rotation during this period. The inert gas can be put under a pressure between 100 mbars and atmospheric pressure. It is also possible for the inert gas in the mold chamber to be put under a pressure greater than atmospheric pressure.

The invention also pertains to a casting mold in which the mold material, at least in the area of the surface which comes in contact with the melt, consists of at least one metal selected from the group tantalum, niobium, zirconium, and/ or their alloys.

It is especially advantageous in this case for the mold material or the shell to contain at least 50 wt. % of tantalum. Additional advantageous properties can be imparted to the mold material by adding metals from the group titanium, hafnium, tungsten, and/or vanadium as alloys to the tantalum. When a mold material with at least 50 wt. % of tantalum is used, it is especially advantageous for the mold material to contain at least one of the metals titanium, zirconium, and tungsten, but the sum of the proportions of these metals should not exceed 30 wt. %. Similar considerations also apply, of course, to the composition of the "shell."

That is, the casting molds do not have to be made of a homogeneous material consisting of the metals or alloys according to the invention; on the contrary, shells or puremetal layers of the cited metals can be provided on a base body, these shells or layers forming the boundary surfaces of the mold cavity, whereas the base body itself consists of a different material.

When the mold cavities of the casting mold are lined by shells of at least one metal, free of nonmetallic constituents, selected from the group tantalum, niobium, zirconium, and/ or their alloys, it is especially advantageous for the thickness of the shells to be at least 2 mm and for the base body of the casting mold to consist of:

(a) either at least one of the metals iron, nickel, and/or their alloys, preferably iron-based alloys; nickel-based alloys; or austenitic, heat-resistant steels; or (b) titanium, titanium alloys, or titanium aluminide; or (c) at least one nonmetallic, oxygen-free material such as graphite or silicon nitride.

Base bodies of the substances cited under (b) and (c) are especially suitable for centrifugal casting molds because of their low mass.

Three exemplary embodiments of the object of the invention are explained in more detail below on the basis of FIGS. 1–7.

BRIEF DESCRIPTION OF THE DRAWING

FIG. 2 shows an axial section through the casting mold according to FIG. 1;

FIG. 3 shows a radial section through the casting mold according to FIG. 2;

FIG. 4 shows an axial section through a valve of an internal combustion engine, produced in a conventional copper mold;

FIG. 5 shows an axial section similar to that of FIG. 4, produced in a casting mold according to the invention;

DETAILED DESCRIPTION OF THE PREFERRED EMBODIMENTS

Figure 1:
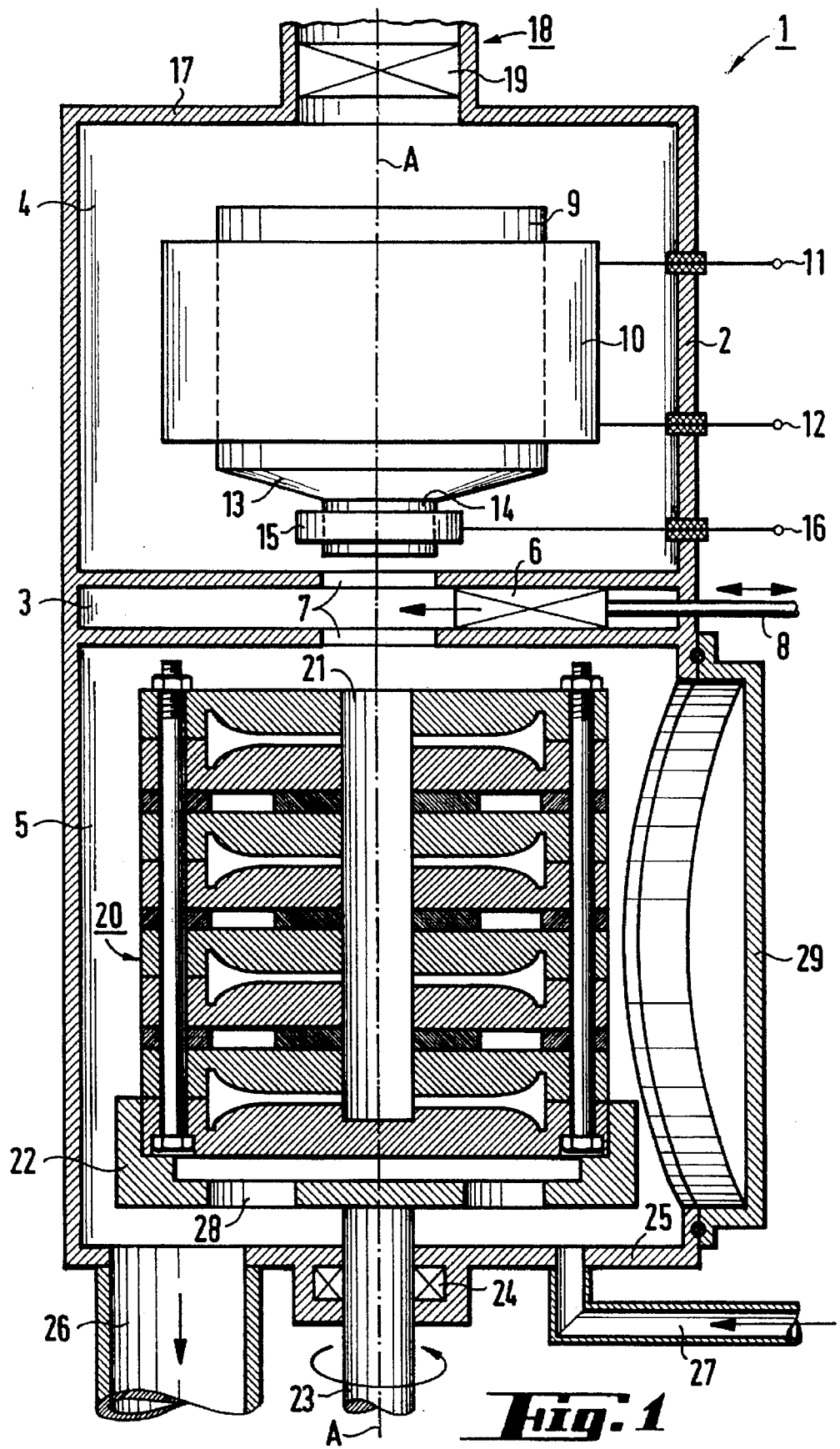
FIG. 1 shows a partial vertical section through a machine with a stationary cold-wall crucible with bottom outlet and a casting mold, which is designed as a centrifugal casting mold with a plurality of mold cavities.

FIG. 1 shows a casting machine 1 with a pressure-tight, gas-tight housing 2, the interior space of which is divided by a slide-valve housing 3 into a melting chamber 4 and a mold chamber 5. In slide-valve housing 3, there is a slide valve 6, by means of which two aligned casting openings 7 can be closed by the action of a drive rod 8.

Inside melting chamber 4 there is a cold-wall crucible 9, the content of which, i.e., the casting material, can be melted by an inductive heating device 10. Two power terminals 11, 12 are used to supply the energy for melting. At the bottom of cold-wall crucible 9 there is an outlet 14, which can be opened and closed by a sealing device, which can be designed as a magnetic coil. The current for sealing device 15 is supplied by way of a terminal 16. A loading device 18, only the lower loading valve 19 of which is indicated, opens out through roof 17 of melting chamber 4. The ways in which a cold-wall crucible of this type are constructed and operated are known and are therefore not described in detail here. Suffice it to say that, in a cold-wall crucible, a so-called "skull" is formed, which prevents the melt from reacting with the crucible material. The connections for a coolant circuit have been omitted for the sake of simplicity.

Figure 6:
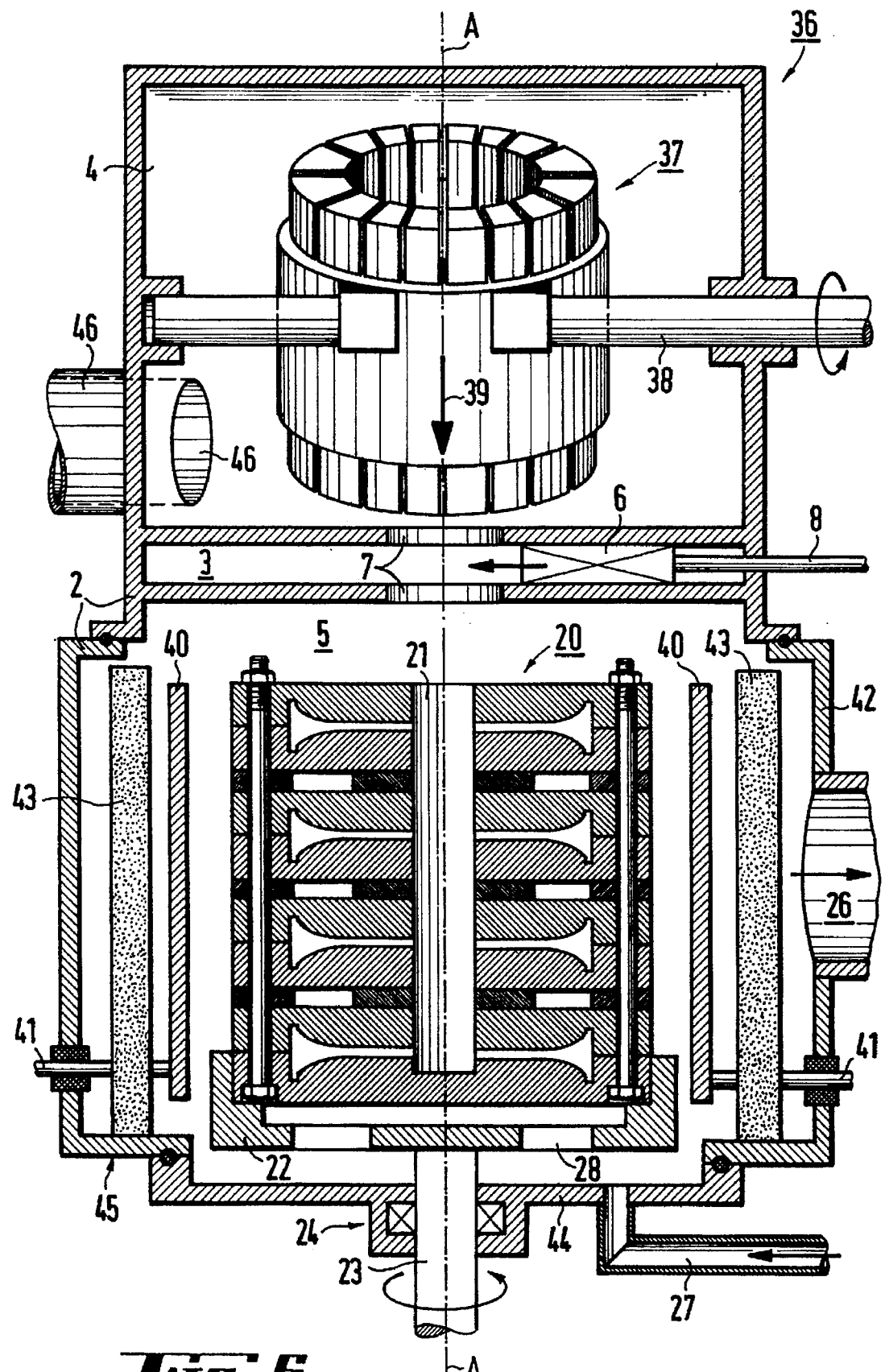
FIG. 6 shows a variant of the machine according to FIG. 1 with a tilting crucible together with the illustration of additional details.

It is obvious that the inductively heated cold-wall crucible described here can also be replaced by a crucible which can be heated by means of an electric arc, an electron beam gun, or a plasma gun. Nor is it necessary for the melt to be poured out through a bottom outlet. It is possible instead to provide an overflow point, i.e., a so-called casting lip, at the upper edge of the crucible. In this case, the cold-wall crucible is advisably suspended in a so-called tilting stand and emptied by way of a rotating axle, which is located near the overflow point. A device of this type is illustrated in FIG. 6.

In mold chamber 5 there is a casting mold 20, the details of which are explained in greater further below on the basis of FIGS. 2 and 3. Here it is enough to say that casting mold 20 has an in-gate 21, which is concentric to a vertical axis A—A, which coincides with the axis of rotation of casting mold 20 and the axis of the crucible. Casting mold 20 is mounted concentrically on a spinner plate 22, which can be driven by a spinning shaft 23, which passes through floor 25 of mold chamber 5 by way of a gas-tight rotary seal 24. Mold chamber 5 is connected to a vacuum line 26, which leads to a vacuum pump unit, which consists of at least one vacuum pump, preferably of a battery of vacuum pumps connected in series, which are designed for different pressure ranges. In addition, a gas line 27, through which inert gas can be introduced into casting mold 20 for the purpose of cooling, also opens into mold chamber 5. Openings 28 in spinner plate 22 facilitate the exchange of cooling gases at the bottom of casting mold 20. Mold chamber 5 is also provided with a door 29, which allows casting mold 20 to be inserted and removed. It should be pointed out that FIG. 1 is only a very schematic diagram of the complete casting machine.

Casting mold 20 according to FIGS. 2 and 3 consists of a stack of disks 30, 31, arranged in pairs as mirror images of one another; these disks enclose mold cavities 32 between them, which, in the present case, correspond to the valve of an internal combustion engine as shown in FIG. 5. Disks 30, 31 are coaxial to axis of rotation A—A, and all mold cavities 32 are connected jointly to in-gate 21, which is also situated on the axis of rotation A—A.

Each pair of disks 30/31 is separated by a spacer 33 from the adjacent pair of disks; spacers 33 also seal off in-gate 21 around the periphery. As a result, only the inner ends of mold cavities 32 are in communication with ingate 21. It is at this point that the ends of the valve shafts are located, and this is the point where they must be separated from the material in in-gate 21 after the end of the casting and cooling phases. The stack-like assembly of disks 30, 31 and spacers 33 is held together by four tension rods 34, spaced equal distances apart around the periphery.

Forty valves according to FIG. 5 can be produced simultaneously in a casting mold 20 according to FIGS. 2 and 3.

Through the action of the cooling gas under continuous rotation of casting mold 20, it is also possible to orient the solidification of the castings, the orientation proceeding from the outside periphery of the casting mold, because the action of the cooling gases is most intense in that area.

Exhaust valves for internal combustion engines according to FIG. 5 were produced in a centrifugal casting mold 20 according to FIGS. 2 and 3. The mold material consisted of an alloy of 90 wt. % of tantalum and 10 wt. % of tungsten. The axial cross section through the valve in FIG. 5 shows no shrink holes, cavities, or other forms of porosity; the surface was also of satisfactory quality.

When disks 30, 31 of the indicated tantalum alloy were replaced by disks of copper or a copper alloy with a high percentage of copper, all of the valves produced from the same titanium alloy had the appearance shown in FIG. 4 with shrink holes and cavities 35 in the polished plane extending almost the entire length of the longitudinal axis.

Example 1

In a machine according to FIG. 1, the alloy 50 Ti 46 Al 2 Cr 2 Nb was melted at a pressure of $10^{-1}$ mbar in melting chamber 4 of cold-wall crucible 9 and then homogenized for 10 minutes after melting was completed. The next step was to pour the melt at a melt temperature of 1,540° C. and at a pressure of $10^{-1}$ mbar into casting mold 20 in mold chamber 5. Casting mold 20 had previously been heated by means of heating device (not shown) to a temperature of 1,400° C. During the casting operation, the casting mold was rotated at a speed of 1,000 rpm. Upon completion of the casting operation, slide valve 6 was closed. About 20 seconds after the end of the casting operation, argon was introduced through gas line 27 into mold chamber 5 until a pressure of 1,000 mbar was reached. The rotation of casting mold 20 was continued until the castings were completely solidified. After about 60 minutes, the castings were completely solidified, and the casting mold was removed from mold chamber 5. The polished axial sections of the individual valves corresponded to those shown in FIG. 5. The polished sections showed no visible pores or shrink holes. As a result, there was no need for any subsequent compaction step such as by means of a HIP process.

Example 2

The experiment according to Example 1 was repeated, but with the difference that the disks from which casting mold 20 was assembled consisted not of a tantalum-tungsten alloy but rather of pure copper. Because of the properties of this material, the disks could not be preheated sufficiently. At the beginning of the casting operation, the mold was therefore at room temperature. After the individual valves had been removed from the copper mold, the polished sections all had the appearance shown in FIG. 4; that is, along the valve axis were typical shrink holes and other porous areas. These valves therefore either had to be discarded or recompacted by means of an HIP process.

FIG. 6 shows a casting machine 36, which represents a variant of the machine according to FIG. 1. The same parts or parts with the same function are designated by the same reference numbers: In melting chamber 4 there is an induction-heated, cold-wall crucible 37, which is designed as a tilting crucible and which can be tilted by means of a tilting shaft 38. The melt can be poured off over the edge in the direction of arrow 39 and through casting openings 7 into casting mold 20. The driven tilting shaft serves simultaneously to supply cooling water and melting current, but the associated lines have been omitted from the drawing.

Casting mold 20 is surrounded by a stationary heating cylinder 40, the power leads 41 of which pass through wall 42 of mold chamber 5; the heating cylinder is surrounded by a cylindrical layer of thermal insulation 43. In this case, mold chamber 5 has a floor 44, which can be lowered together with spinner plate 22 and its drive. This is done after the chamber has been flooded and after sufficient cooling has occurred. As a result, the top surface of casting mold 20 arrives underneath lower edge 45 of mold chamber 5, so that casting mold 20 can be lifted from spinner plate 22. To keep melting chamber 4 under continuous vacuum, this chamber is connected to an additional vacuum line 46 with a battery of vacuum pumps.

Figure 7:
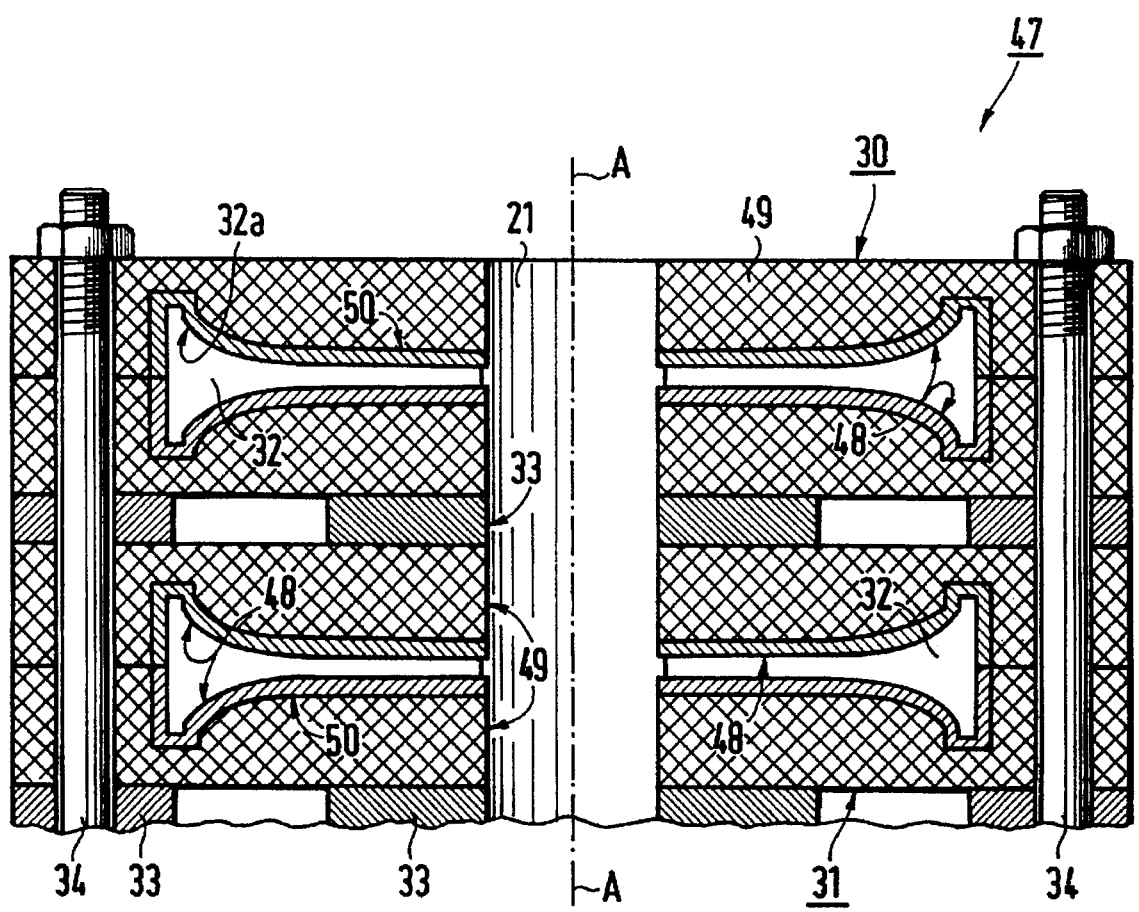
FIG. 7 shows an enlarged axial section through a casting mold, in which the base material of the casting mold consists of a different material.

FIG. 7 shows the upper part of a reusable casting mold 47 similar to casting mold 20 according to FIG. 2, but with the difference that mold cavities 32 in disks 30, 31 are lined by shells 48 (shaded areas), which are made of a metal, free of nonmetallic constituents, selected from the group tantalum, niobium, zirconium and/or their alloys. This means that shells 48, each independently, are dense, compact, homogeneous, and tightly cohesive, and that therefore they cannot be removed by water jets, brushing, or the like.

The terms "shell" and "layer" are meant to imply that the metal of which they are made can either cohere tightly to a base body 49 (crosshatched), which gives the disks their intrinsic strength, or be inserted replaceably into a base body 49. Replaceable shells 48 can, for example, be produced either by casting, mechanical machining, or by explosion-forming; shells 48 permanently joined to base body 49 can be produced by, for example, flame-spraying, electroplating, sintering, etc.

This base body 49 can consist of at least one of the metals iron, nickel, titanium, or their alloys, as well as of titanium aluminide, but preferably of iron-based alloys; nickel-based alloys; austenitic, heat-resistant steels; or the previously cited titanium, titanium alloys, or titanium aluminide Base body 49 can also consist, however, of at least one nonmetallic, oxygen-free material such as, for example, graphite or silicon nitride.

For centrifugal casting molds, titanium , titanium alloys, titanium aluminides, graphite, and/or silicon nitride are especially suitable as materials for base body 49, because the mass of base body 49 accounts for most of the weight of the rotating system, and therefore the extent of the rotating masses can be minimized. In addition, these materials, especially in conjunction with shells 48, are extremely strong and heat-resistant.

Base body 49 is provided with recesses 50, into which shells 48 can be laid or embedded. The surface of the shells or of mold cavity 32 coming in contact with the melt is designated 32a.

Metal base bodies 49 can, for example, be produced by casting and/or mechanical machining or working; nonmetallic base bodies 49 can be produced by, for example, pressing in molds followed by sintering and possibly by a subsequent mechanical processing.

In the foregoing description, it will be understood that the term tantalum-based alloy refers to an alloy containing at least 50% by weight of tantalum. In the preferred embodiment, the surface of the casting mold has at least 50% by weight Ta, Nb or Zr, or at least 50% by weight Ta+Nb, Ta+Zr, or Nb+Zr, or at least 50% by weight Ta+Nb+Zr.

We claim:

1. Process for production of castings comprising
   providing a reusable casting mold having a surface which comes in contact with molten metal, said surface consisting of at least one metal selected from the group consisting of tantalum, tantalum alloys, niobium, niobium alloys, zirconium, and zirconium alloys, and
   casting in said mold a melt of a reactive metal selected from the group consisting of titanium and titanium alloys.

2. Process as in claim 1 wherein said surface consists of a tantalum alloy.

3. Process as in claim 1 further comprising rotating said mold while said reactive metal therein solidifies.

4. Process as in claim 1 further comprising preheating said mold prior to casting.

5. Process as in claim 4 wherein said melt has a liquidus temperature and a solidus temperature, said mold being preheated to a temperature below said liquidus temperature.

6. Process as in claim 5 wherein said mold is preheated to a temperature between 800° C. and the solidus temperature.

7. Process as in claim 1 wherein said melt is cast in said mold in a closed mold chamber at a pressure of less than 100 mbars.

8. Process as in claim 7 further, comprising introducing an inert gas into said mold chamber subsequent to casting.

9. Process as in claim 8 wherein said inert gas is at a pressure between 100 mbars and atmospheric pressure.

10. Process as in claim 8 wherein said inert gas is at a pressure greater than atmospheric pressure.

11. Method as in claim 1 wherein said casting is performed in the absence of water cooling of said mold.

12. Method as in claim 1 wherein said casting mold comprises a base body and a shell on said base body, said shell comprising said surface which comes in contact with molten metal, said base body consisting of metal excluding copper.

13. Process as in claim 1 wherein said process is a centrifugal casting process wherein said mold is rotated during casting.

* * * * *